(12) United States Patent
Iwahashi et al.

(10) Patent No.: US 8,000,883 B2
(45) Date of Patent: Aug. 16, 2011

(54) CONTROL APPARATUS AND METHOD FOR AIR-FUEL RATIO SENSOR

(75) Inventors: Takeshi Iwahashi, Toyota (JP); Motoki Ohtani, Toyota (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 442 days.

(21) Appl. No.: 12/301,833

(22) PCT Filed: May 23, 2007

(86) PCT No.: PCT/IB2007/001327
§ 371 (c)(1),
(2), (4) Date: Nov. 21, 2008

(87) PCT Pub. No.: WO2007/138412
PCT Pub. Date: Dec. 6, 2007

(65) Prior Publication Data
US 2010/0242445 A1   Sep. 30, 2010

(30) Foreign Application Priority Data
May 24, 2006   (JP) ................................ 2006-144090

(51) Int. Cl.
*F01N 11/00* (2006.01)
(52) U.S. Cl. .............. 701/109; 701/113; 123/142.5 E; 123/676; 60/286
(58) Field of Classification Search .............. 701/109, 701/113; 123/675, 685, 686, 689, 142.5 E; 60/286
See application file for complete search history.

(56) References Cited

U.S. PATENT DOCUMENTS

| 4,655,182 | A   | * | 4/1987  | Nakano et al. ............. 123/179.1 |
| 5,353,774 | A   | * | 10/1994 | Furuya .......................... 123/685 |
| 5,492,107 | A   | * | 2/1996  | Furuya .......................... 123/686 |
| 6,935,101 | B2  | * | 8/2005  | Morinaga et al. .............. 60/284 |
| 7,193,178 | B2  | * | 3/2007  | Sell et al. ....................... 219/202 |
| 7,526,914 | B2  | * | 5/2009  | Nakano ........................... 60/276 |
| 7,743,759 | B2  | * | 6/2010  | Aoki ............................. 123/672 |
| 2003/0052016 | A1 | * | 3/2003  | Lin et al. ....................... 205/785 |
| 2009/0150057 | A1 | * | 6/2009  | Adams et al. ................. 701/109 |

FOREIGN PATENT DOCUMENTS

| DE | 43 00 530 A1 | 7/1994 |
| DE | 199 28 561 A1 | 1/2001 |
| JP | 11-082113 A | 3/1999 |
| JP | 2000-097902 A | 4/2000 |
| JP | 2001-021524 A | 1/2001 |
| JP | 2001-041923 A | 2/2001 |
| JP | 2001-073827 A | 3/2001 |

(Continued)

*Primary Examiner* — Erick Solis
(74) *Attorney, Agent, or Firm* — Sughrue Mion, PLLC

(57) ABSTRACT

The ECU executes a program that includes the steps of: calculating the temperature Texp of the wall surface of the exhaust port and the temperature Tsen of the wall surface of the inner cover covering the zirconia element of the A/F sensor (S110); heating the zirconia element by the heater (S130) when at least one of the condition that the temperature Texp is equal to or higher than the first threshold and the condition that the temperature Tsen is equal to or higher than the second threshold is in effect (S120: YES); and prohibiting the heating of the zirconia element by the heater (S140) when the temperature Texp is lower than the first threshold and the temperature Tsen is lower than the second threshold (S120: NO).

12 Claims, 8 Drawing Sheets

FOREIGN PATENT DOCUMENTS

| | | |
|---|---|---|
| JP | 2002-048749 A | 2/2002 |
| JP | 2002-256949 A | 9/2002 |
| JP | 2003-049700 A | 2/2003 |
| JP | 2003-227400 A | 8/2003 |
| JP | 2004-100483 A | 4/2004 |
| JP | 2006-207424 A | 8/2006 |

* cited by examiner

CONTROL APPARATUS AND METHOD FOR AIR-FUEL RATIO SENSOR

BACKGROUND OF THE INVENTION

1. Field of the Invention

The invention relates to a control apparatus and a control method for air-fuel ratio sensors, and particularly to a technology for heating a sensing element of an air-fuel ratio sensor.

2. Description of the Related Art

A technology is known in which the air-fuel ratio of an internal combustion engine is detected by an air-fuel ratio sensor and the internal combustion engine is controlled to operate at a desired air fuel ratio. Air-fuel ratio sensors detect air-fuel ratios by utilizing the electromotive force of a zirconia element. To activate such an air-fuel ratio sensor, its zirconia element needs to be heated. Therefore, in general, an air-fuel ratio sensor has a heater for heating its zirconia element.

Meanwhile, when the temperature in the exhaust passage in which an air-fuel ratio sensor is provided is low, water droplets exist in the exhaust passage. If the water droplets contact the zirconia element of the air-fuel ratio sensor while it is being heated, it may damage the zirconia element. Therefore, the heating of the zirconia element is carried out when the water droplets are considered to be no longer present in the exhaust passage.

JP-A-2003-227400 describes a control apparatus for controlling the temperature of an air-fuel ratio sensor, which enables early activation of the air-fuel ratio sensor without causing cracking of the sensing element. The temperature control apparatus described in this publication includes a switching portion. In operation, this switching portion keeps a heat-applied portion, which is a portion to which heat of an amount necessary for enabling the early activation of the air-fuel ratio sensor is applied, in a preheated state until the temperature of a protection portion for protecting the sensor element reaches a predetermined value. When the temperature of the protection portion reaches the predetermined value, the switching portion places the heat-applied portion in a heated state in which the heat-applied portion is heated by a larger amount of heat than it is in the preheated state.

According to the temperature control apparatus described in JP-A-2003-227400, the heat-applied portion is preheated until the temperature of the protection portion located close to the sensing element, which temperature thus accurately reflects whether and how much the sensing element is wet, reaches the predetermined value, that is, until the sensing element is no longer wet, and thereafter the heat-applied portion is placed in the heated state where a larger amount of heat is applied to the heat-applied portion than in the preheated state. Thus, it is possible to activate the sensing element at an earlier time while reliably preventing cracking of the sensing element, which may otherwise be caused if the sensing element in wet condition is rapidly heated.

In the mean time, in some internal combustion engines, the temperature of exhaust gas is increased by retarding the ignition timing so as to accelerate the warming-up of a catalyst used to purify exhaust gas. In this case, a protection cover for protecting the sensing element of the air-fuel ratio sensor increases quickly. On the other hand, in the state where the retardation of the ignition timing is prohibited, the increase in the temperature of the protection cover is sluggish. Therefore, if preheating of the air-fuel ratio sensor is continued until the temperature of a protection member (protection cover) for protecting the sensing element reaches a predetermined value as in the case of the temperature control apparatus described in JP-A-2003-227400, the activation of the air-fuel ratio sensor may be delayed unnecessarily.

SUMMARY OF THE INVENTION

The invention provides a control apparatus and a control method for an air-fuel ratio sensor, which enable early activation of the air-fuel ratio sensor.

A first aspect of the invention relates to a control apparatus that controls an air-fuel ratio sensor that is provided in an exhaust passage of an internal combustion engine and has a protection member covering a sensing element. The control apparatus includes: calculating means for calculating the temperature in the exhaust passage and the temperature of the protection member; and heating controlling means for controlling heating means for heating the sensing element, the heating means being provided in the air-fuel ratio sensor. The heating controlling means controls the heating means not to heat the sensing element when the temperature in the exhaust passage is lower than a first threshold and the temperature of the protection member is lower than a second threshold and controls the heating means to heat the sensing element when the temperature in the exhaust passage is higher than the first threshold and/or the temperature of the protection member is higher than the second threshold.

According to the control apparatus of the first aspect of the invention, the sensing element of the air-fuel ratio sensor is heated by the heating means. When the temperature of the protection member covering the sensing element is high, the water droplets present in the exhaust passage would evaporate by contacting the protection member before reaching the sensor element. Therefore, if the heating of the sensing element is started after the temperature of the protection member becomes high, it reduces the possibility that water droplets would contact the sensing element while it is being heated. Because the air-fuel ratio sensor is provided in the exhaust passage, the higher the temperature of exhaust gas, the more quickly the temperature of the protection member increases. Therefore, in the state where the ignition timing of the internal combustion engine is retarded, the temperature of exhaust gas is high and thus the temperature of the protection member increases quickly. On the other hand, in the state where the retardation of the ignition timing is prohibited, the temperature of exhaust gas is not high, and therefore the increase in the temperature of the protection member is sluggish. However, water droplets disappear when the temperature in the exhaust passage is high even if the temperature of the protection member is not high. As such, the heating means is controlled not to heat the sensing element when the temperature in the exhaust passage is lower than the first threshold and the temperature of the protection member is lower than the second threshold and to heat the sensing element when the temperature in the exhaust passage is higher than the first threshold and/or the temperature of the protection member is higher than the second threshold. As a result, the heating of the sensing element can be started at the earlier of the time the temperature in the exhaust passage exceeds the first threshold and the time the temperature of the protection member exceeds the second threshold. Thus, the air-fuel ratio sensor can be activated at an earlier time.

The control apparatus according to the first aspect of the invention may further include exhaust gas temperature estimating means for estimating the temperature of exhaust gas of the internal combustion engine and may be such that the calculating means calculates at least one of the temperature in the exhaust passage and the temperature of the protection member based on the temperature of the exhaust gas.

According to the control apparatus described above, the exhaust gas temperature estimating means estimates the temperature of exhaust gas. Because the temperature in the exhaust passage and the temperature of the protection member are strongly influenced by the temperature of exhaust gas. Therefore, at least one of the temperature in the exhaust passage and the temperature of the protection member can be calculated based on the temperature of exhaust gas. As such, the temperature in the exhaust passage and/or the temperature of the protection member can be accurately calculated.

The control apparatus according to the first aspect of the invention may be such that the exhaust gas temperature estimating means estimates the temperature of the exhaust gas based on the ignition timing of the internal combustion engine and the amount of intake air for the internal combustion engine.

The temperature of exhaust gas is strongly influenced by the ignition timing of the internal combustion engine and the amount of intake air for the internal combustion engine. Therefore, the control apparatus described above estimates the temperature of exhaust gas based on the ignition timing and the intake amount. Thus, the temperature of exhaust gas can be accurately calculated.

A second aspect of the invention relates to a control apparatus for an air-fuel ratio sensor which includes: exhaust gas temperature estimating means for estimating the temperature of exhaust gas of the internal combustion engine; coolant temperature detecting means for detecting the temperature of the coolant of the internal combustion engine; a counter that increments its count according to the temperature of the exhaust gas; and heating controlling means for controlling heating means for heating the sensing element, the heating means being provided in the air-fuel ratio sensor. The heating controlling means controls the heating means to heat the sensing element when the count of the counter is larger than a third threshold and/or the temperature of the coolant is higher than a fourth threshold.

The control apparatus according to the second aspect of the invention may be such that the amount by which the counter increments the count is set larger when the ignition timing of the internal combustion engine is at a first point than when the ignition timing is at a second point that is earlier than the first point.

A third aspect of the invention relates to a control method for an air-fuel ratio sensor that is provided in an exhaust passage of an internal combustion engine and has a protection member covering a sensing element. In this control method, the temperature of exhaust gas is estimated based on the amount of intake air for the internal combustion engine and the ignition timing of the internal combustion engine, the temperature in the exhaust passage and the temperature of the protection member are calculated based on the temperature of the exhaust gas, and the sensing element is heated when the temperature in the exhaust passage is higher than a first threshold and/or the temperature of the protection member is higher than a second threshold.

In addition to the respective arrangements and modifications presented above, the internal combustion engine incorporating the control apparatus according to the first aspect of the invention may be an internal combustion engine in which, when the internal combustion engine is at a low temperature, the ignition timing is retarded to warm up the catalyst provided in the exhaust passage.

In this case, too, early activation of the air-fuel ratio sensor can be achieved.

BRIEF DESCRIPTION OF THE DRAWINGS

The foregoing and further objects, features and advantages of the invention will become apparent from the following description of preferred embodiments with reference to the accompanying drawings, wherein like numerals are used to represent like elements and wherein.

DETAILED DESCRIPTION OF THE EXEMPLARY EMBODIMENTS

Figure 1:
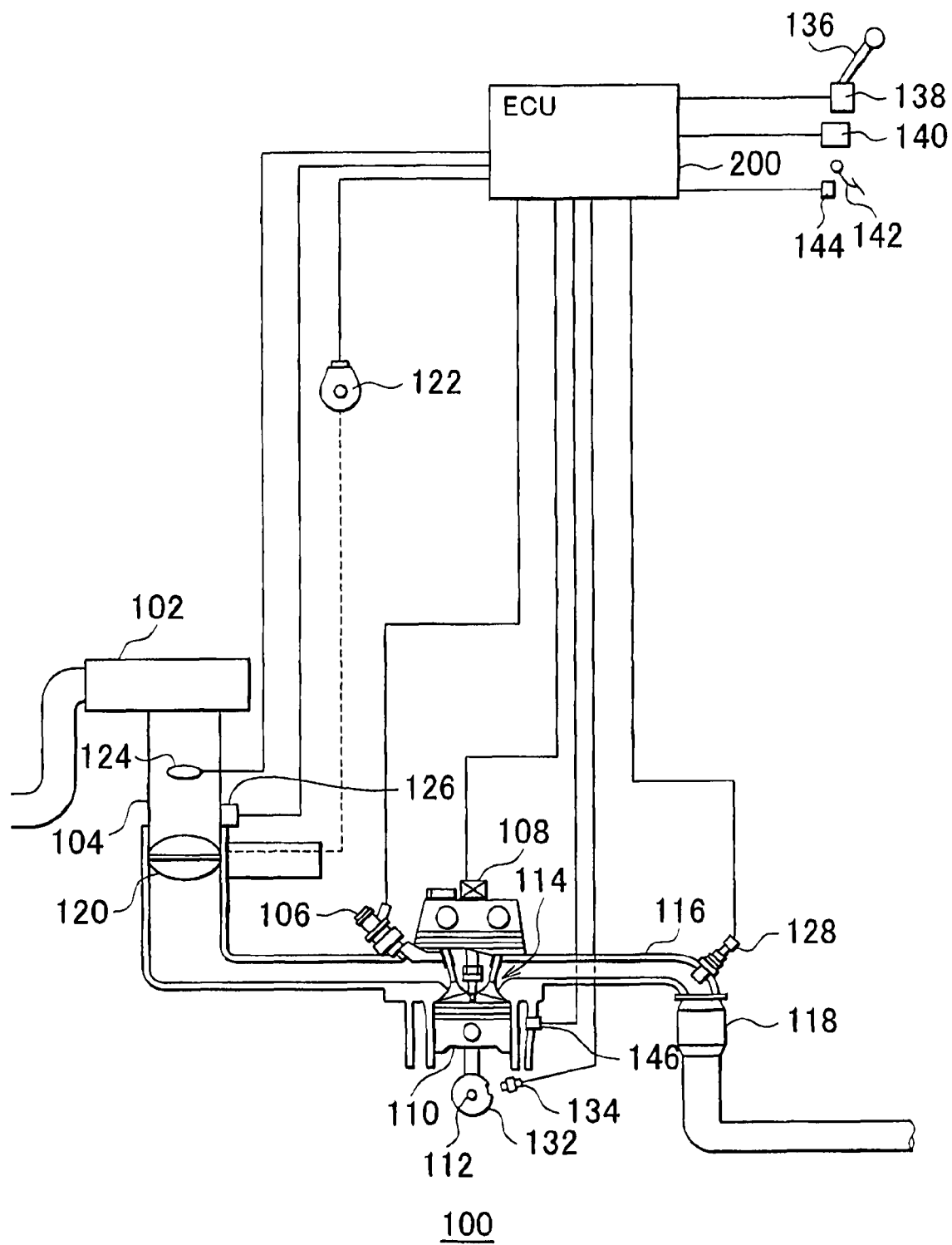
FIG. 1 is a control block diagram showing the configuration of the engine of the vehicle incorporating the air-fuel ratio sensor control apparatus according to the first exemplary embodiment of the invention.

Hereinafter, exemplary embodiments of the invention will be described with reference to the accompanying drawings. In the flowing descriptions, like components and elements will be denoted by like numerals. Since their names and functions are the same, their descriptions will not be repeated.

First Exemplary Embodiment

An engine 100 of a vehicle incorporating an air-fuel ratio sensor control apparatus according to the first exemplary embodiment of the invention will be described with reference to FIG. 1. The vehicle runs on the drive power from the engine 100. The engine 100 is controlled by an ECU (Electronic Control Unit) 200. The air-fuel ratio sensor control apparatus of the first exemplary embodiment is realized by, for example, the programs executed by the ECU 200.

Air is drawn into the engine 100 via an air cleaner 102 and then proceeds in an intake pipe 104. Then, the air is mixed up with the fuel injected from an injector 106 and drawn into each combustion chamber of the engine 100 in the form of an air-fuel mixture. Then, the air-fuel mixture is ignited by a spark plug 108 and thus combusted in the combustion chamber. The combustion of the air-fuel mixture in the combustion chamber forces a piston 110 down and it turns a crankshaft 112. The combusted air-fuel mixture, that is, the exhaust gas proceeds in an exhaust port 114 and an exhaust manifold 116. Then, the exhaust gas is purified at a catalyst 118 and thereafter discharged to the outside of the vehicle.

The catalyst 118 is a three-way catalyst. The purification capability of the catalyst 118 for purifying exhaust gas, i.e., for removing NOx, CO, and HC, can work when the catalyst 118 is activated.

The amount of intake air for the engine 100 is adjusted by a throttle valve 120. The opening degree of the throttle valve 120 is detected by a throttle sensor 122. The throttle sensor 122 transmits signals indicating its detection results to the ECU 200.

The amount of intake air for the engine 100 is detected by an air-flow meter 124, and the intake pressure is detected by an intake pressure sensor 126. The air-flow meter 124 and the intake pressure sensor 126 transmit signals indicating their detection results to the ECU 200.

Figure 2:
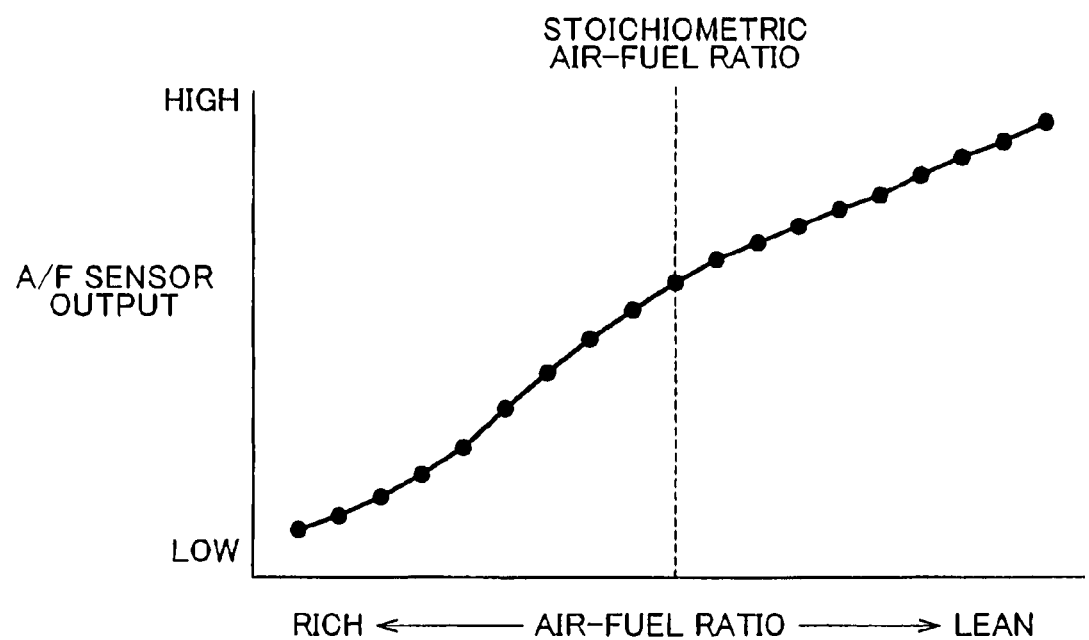
FIG. 2 is a chart illustrating the output characteristics of the air-fuel ratio sensor.

On the upstream side of the catalyst 118, an air-fuel ratio sensor (will be referred to as "A/F sensor") 128 is provided to detect the air-fuel ratio of the engine 100. Referring to FIG. 2, the A/F sensor 128 outputs voltages proportional to the air fuel ratios. The voltage output from the A/F sensor 128 increases as the air-fuel ratio becomes leaner (i.e., as the air-fuel ratio increases).

Note that the A/F sensor 128 may be replaced by an $O_2$ sensor, and an $O_2$ sensor may be provided downstream of the catalyst 118 as well as the A/F sensor provided upstream of the catalyst 118, and A/F sensors or $O_2$ sensors may be provided on both the upstream and downstream sides of the catalyst 118.

The A/F sensor 128 outputs voltages having the characteristic described above when the A/F sensor 128 has already been activated by being sufficiently heated. The signals indicating the voltages of the A/F sensor 128 are transmitted to the ECU 200. The ECU 200 determines the air-fuel ratio of the engine 100 based on the voltage signals transmitted from the A/F sensor 128.

Back to FIG. 1, a crank position sensor 134 is provided at a position facing a timing rotor 132 provided on the crank shaft 112. The engine speed of the engine 100 (i.e., the rotation speed of the crank shaft 112) is determined based on the pulse signals from the crank position sensor 134. That is, the crank position sensor 134 transmits the pulse signals to the ECU 200, and the ECU 200 determines the engine speed of the engine 100 based on the transmitted pulse signals.

In addition, a position sensor 138 that detects the position of a shift lever 136, a vehicle speed sensor 140 that detects the speed of the vehicle, and an accelerator operation amount sensor 144 that detects the operation amount of an accelerator pedal 142 are connected to the ECU 200. Further, a temperature sensor 146 that detects a coolant temperature WT in the engine 100 is also connected to the ECU 200.

A CPU (Central Processing Unit) of the ECU 200, which is not shown in the drawings, performs computations based on the received signals and various programs and maps stored in the memory, not shown in the drawings, so as to achieve desired operation conditions of the engine 100.

In the first exemplary embodiment, the ECU 200 performs a feedback control that controls the air-fuel ratio of the engine 100 based on the air-fuel ratios detected by the A/F sensor 128 (i.e., the voltages output from the A/F sensor 128).

The ECU 200 performs a rapid warm-up control that rapidly warms the catalyst 118 up by retarding the ignition timing when the coolant temperature WT of the engine 100 is lower than a threshold, such as immediately after the start of the engine 100.

Figure 3:
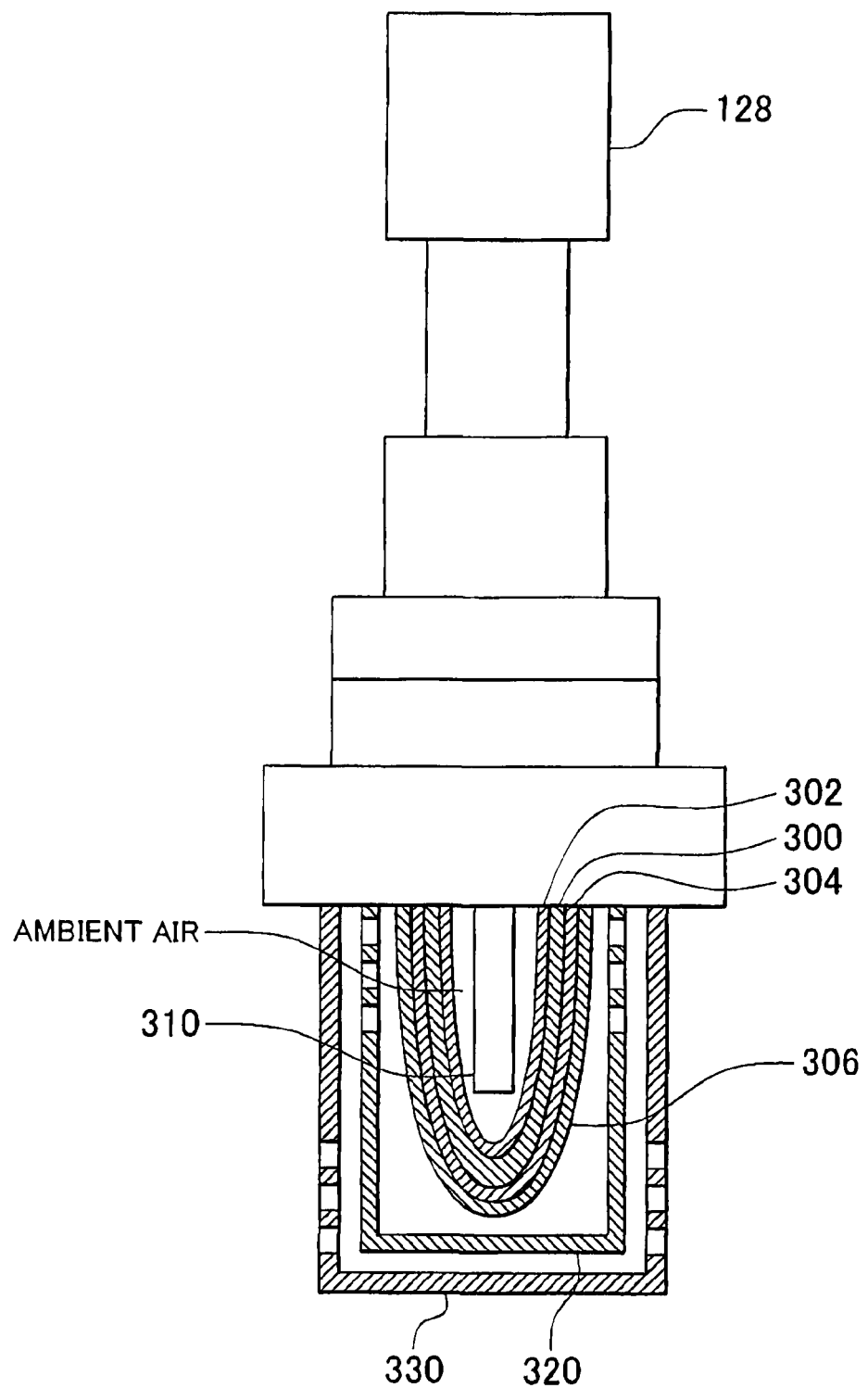
FIG. 3 is a view showing the air-fuel ratio sensor.

The A/F sensor 128 will be further described with reference to FIG. 3. The A/F sensor 128 in the first exemplary embodiment is a cup-shaped A/F sensor. Note that it may alternatively be a multi-layered A/F sensor.

The A/F sensor 128 has a zirconia element 300 that is a solid electrolyte, an ambient-air-side electrode 302 that is provided on the inner surface of the zirconia element 300, an exhaust-gas-side electrode 304 that is provided on the outer surface of the zirconia element 300, a ceramic coating 306 that covers the exhaust-gas-side electrode 304, and a heater 310 that is used to heat the zirconia element 300.

Further, the A/F sensor 128 has an inner cover 320 and an outer cover 330 that cover and thereby protect the zirconia element 300, the ambient-air-side electrode 302, the exhaust-gas-side electrode 304, and the ceramic coating 306.

The zirconia element 300 outputs the voltage corresponding to the difference between the oxygen concentration at the inner surface of the zirconia element 300 and that at the outer surface when the zirconia element 300 is activated, that is, when it is at a high temperature. The larger the difference in the oxygen concentration, the higher the output voltage of the zirconia element 300 becomes. The zirconia element 300 is activated by being heated by the heater 310.

The ambient-air-side electrode 302 and the exhaust-gas-side electrode 304 are both made of platinum. Platinum has the catalytic effect of making the oxygen in the exhaust gas and CO bond to each other. The voltage output of the A/F sensor 128 increases as the oxygen concentration at the exhaust gas side of the zirconia element 300 decreases and thus the difference in the oxygen concentration between the ambient air side and the exhaust gas side of the zirconia element 300 increases.

Multiple small holes through which exhaust gas flows are formed in the inner cover 320 and the outer cover 330, respectively. In the first exemplary embodiment, the inner cover 320 and the outer cover 330 are arranged such that the small holes in the inner cover 320 and those in the outer cover 330 do not overlap each other. Note that the inner cover 320 and the outer cover 330 may alternatively be arranged such that the small holes in the inner cover 320 and those in the outer cover 330 overlap each other.

Next, the control algorithms of the programs that are executed by the ECU 200, which corresponds to the air-fuel ratio sensor control apparatus of the first exemplary embodiment, will be described with reference to FIG. 4.

Figure 5:
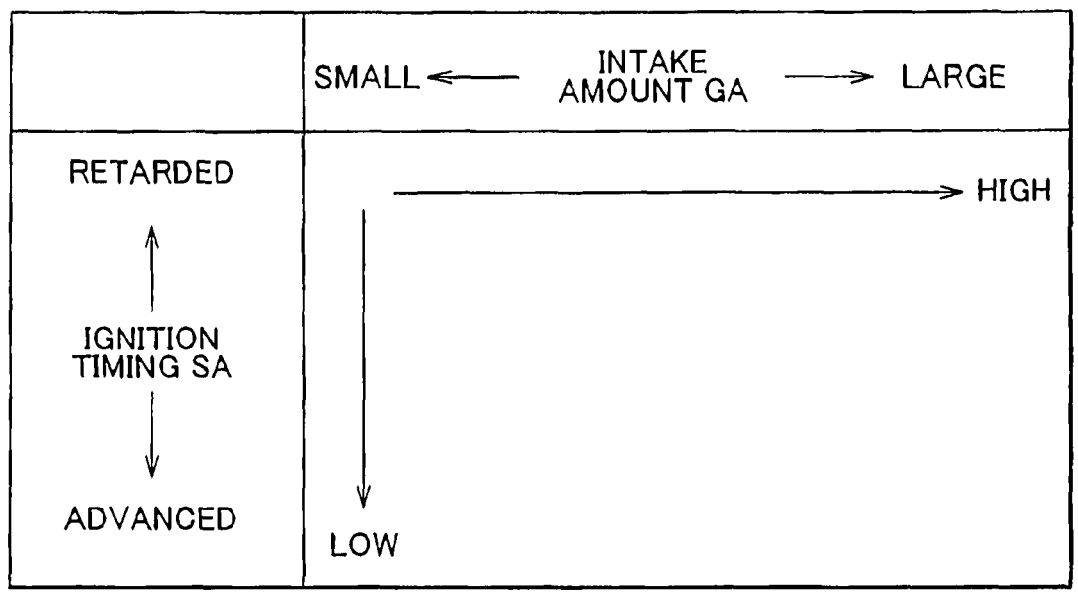
FIG. 5 is a map used to calculate the temperature of exhaust gas.

First, in step 100 ("step" will hereinafter be abbreviated to "S"), the ECU 200 calculates a temperature EXtemp of exhaust gas based on an amount GA of intake air for the engine 100 and an ignition timing SA of the engine 100. The temperature EXtemp of exhaust gas is calculated using a map, such as the one shown in FIG. 5, in which the intake amount GA and the ignition timing SA are used as parameters. Referring to FIG. 5, the temperature EXtemp of exhaust gas is calculated such that it increases as the intake amount GA increases and as the ignition timing SA is retarded.

Figure 4:
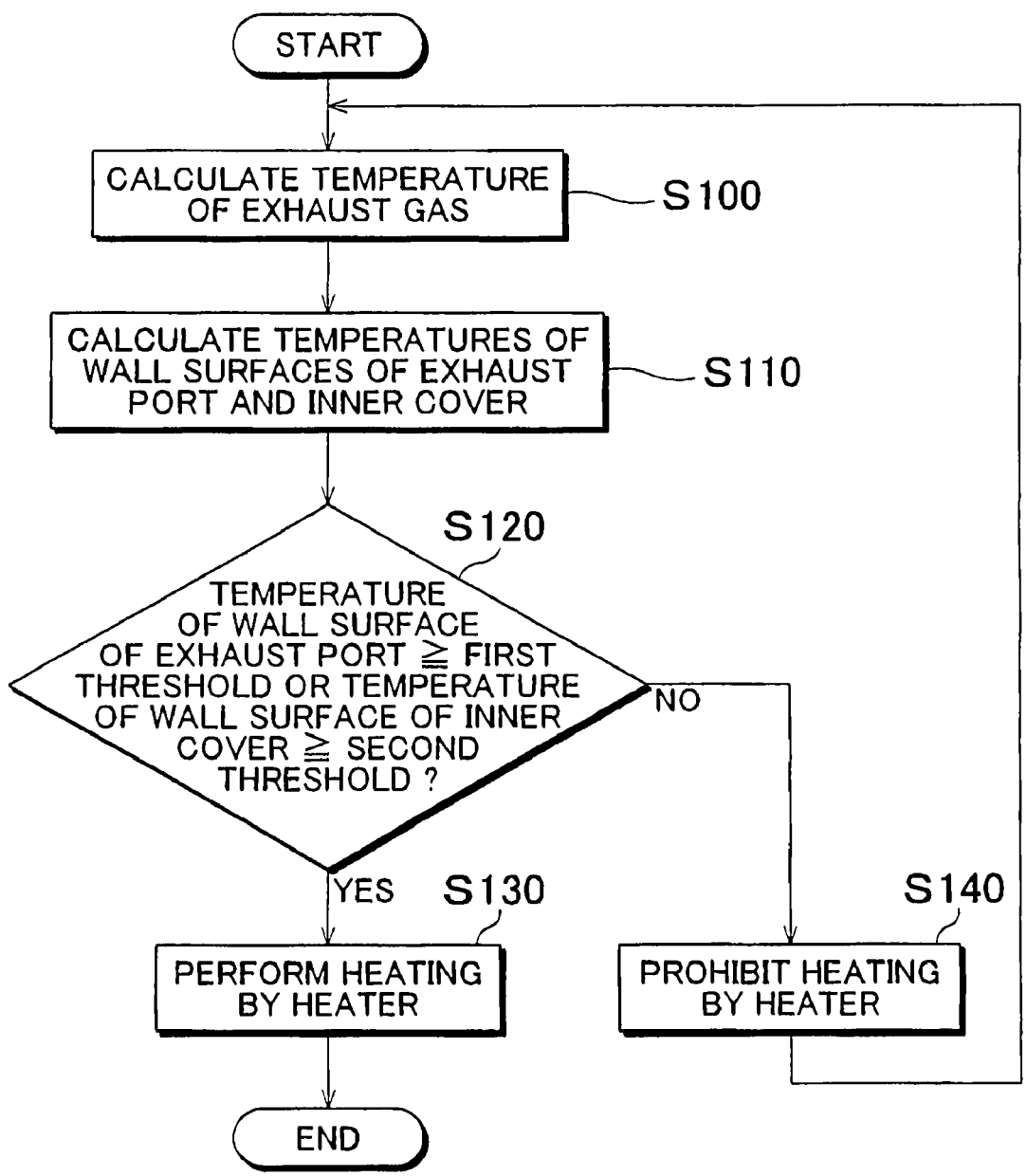
FIG. 4 is a flowchart illustrating the control algorithm of the program executed by the ECU of the air-fuel ratio sensor control apparatus according to the first exemplary embodiment of the invention.

Back to FIG. 4, in S110, the ECU 200 calculates (detects) a temperature Texp of the wall surface of the exhaust port 114 and a temperature Tsen of the outer wall surface of the inner cover 320 (i.e., the wall surface of the inner cover 320 on the side opposite from where the zirconia element 300 is located) based on the temperature EXtemp of exhaust gas.

The temperature Texp of the wall surface of the exhaust port 114 is calculated by the expression (1) shown below:

$$Texp1 = Texp0 + (EXtemp - Texp0) \times \alpha + WT + Y \quad (1)$$

where "Texp 1" represents the temperature of the wall surface of the exhaust port 114 that is calculated in the present cycle of the control routine and "Texp 0" represents the same temperature that was calculated in the last cycle of the control routine, "WT" represents the temperature of the coolant of the engine 100, and α and Y are coefficients that have been determined based on the results of experiments and simulations. The initial value of the temperature Texp of the wall surface of the exhaust port 114 is set to the lower of the temperature WT of the coolant and the ambient temperature.

The temperature Tsen of the wall surface of the inner cover 320 is calculated by the expression (2) shown below:

$$Tsen1 = Tsen0 + (EXtemp - Tsen0) \times \beta \qquad (2)$$

where "Tsen1" represents the temperature of the wall surface of the inner cover 320 that is calculated in the present cycle of the control routine, "Tsen0" represents the same temperature that was calculated in the last cycle of the control routine, and $\beta$ is a coefficient that has been determined based on the results of experiments and simulations. The initial value of the temperature Tsen of the wall surface of the inner cover 320 is set to the lower of the temperature WT of the coolant and the ambient temperature.

Next, in S120, the ECU 200 determines whether at least one of the condition that the temperature Texp of the wall surface of the exhaust port 114 is equal to or higher than a first threshold and the condition that the temperature Tsen of the wall surface of the inner cover 320 is equal to or higher than a second threshold is in effect.

The first threshold is set to the temperature reflecting the dew point of water droplets (water content). The second threshold is set to the temperature at which, if water droplets contact the wall surface of the inner cover 320, the water droplets would evaporate in a moment. The temperature set as the first threshold may be the dew point of water droplets or above.

When at least one of the condition that the temperature Texp of the wall surface of the exhaust port 114 is equal to or hither than the first threshold and the condition that the temperature Tsen of the wall surface of the inner cover 320 is equal to or higher than the second threshold is in effect (S120: YES), the ECU 200 then proceeds to S130. If none of the two conditions is in effect (S120: NO), conversely, the ECU 200 proceeds to S140.

In S130, the ECU 200 heats the zirconia element 300 using the heater 310, after which the present cycle of the control routine ends. On the other hand, in S140, the ECU 200 prohibits the heating of the zirconia element 300 by the heater 310, after which the ECU 200 returns to S100.

Next, a description will be made of the operation of the ECU 200 which has the foregoing structure and executes the control routine described above and which corresponds to the control apparatus according to the first exemplary embodiment.

Figure 6:
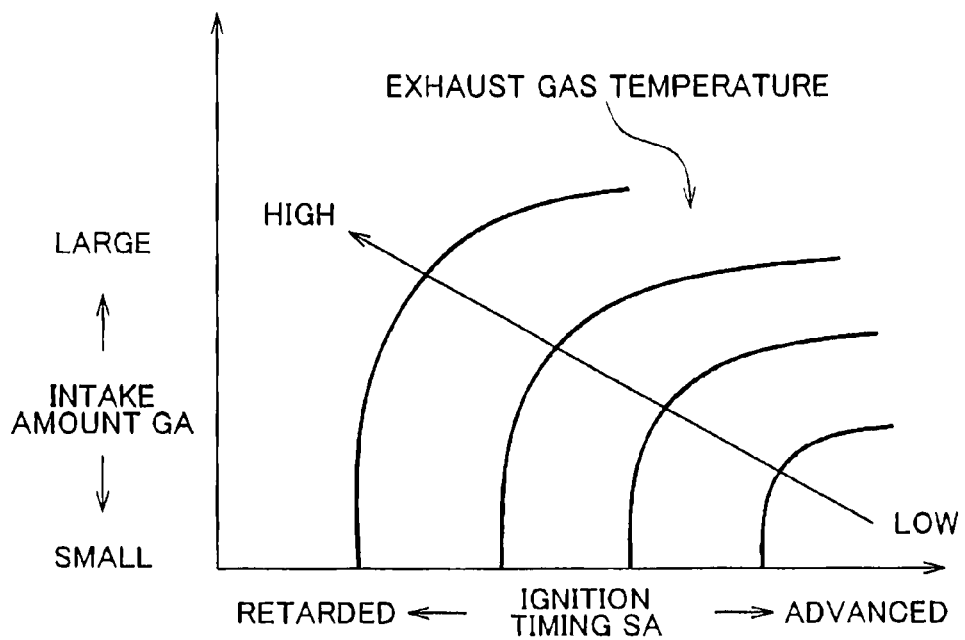
FIG. 6 is a chart illustrating how the temperature of exhaust gas changes.

After the start of the engine 100, the temperature EXtemp of exhaust gas is calculated (S100). As shown in FIG. 6, the temperature EXtemp of exhaust gas tends to increase as the amount GA of the intake air for the engine 100 increases and as the ignition timing SA is retarded. Thus, the temperature EXtemp of exhaust gas is calculated based on the amount GA of intake air for 100 and the ignition timing SA of the engine 100.

Then, the temperature Texp of the wall surface of the exhaust port 114 and the temperature Tsen of the wall surface of the inner cover 320 are calculated based on the temperature EXtemp of exhaust gas (S110).

The temperature Texp of the wall surface of the exhaust port 114 is influenced by the temperature WT of the coolant, as well as by the temperature EXtemp of exhaust gas. Therefore, the temperature Texp of the wall surface of the exhaust port 114 is calculated in consideration of the temperature WT of the coolant, as indicated in the foregoing expression (1).

On the other hand, the temperature Tsen of the wall surface of the inner cover 320 of the A/F sensor 128 provided in the exhaust manifold 116 is not influenced by the coolant temperature WT of the coolant. Therefore, the temperature Tsen of the wall surface of the inner cover 320 is calculated without considering the temperature WT of the coolant, as indicated in the foregoing expression (2).

If the temperature Texp of the wall surface of the exhaust port 114 is equal to or higher than the first threshold, it indicates that the residual water droplets have already evaporated. In this state, therefore, it is considered that the zirconia element 300 would not contact any water droplets.

Also, if the temperature Tsen of the wall surface of the inner cover 320 of the A/F sensor 128 is equal to or higher than the second threshold, it indicates that the water droplets in the exhaust manifold 116 would evaporate when they contact the inner cover 320. In this state, it is considered that the zirconia element 300 would not contact any water droplets.

Figure 7:
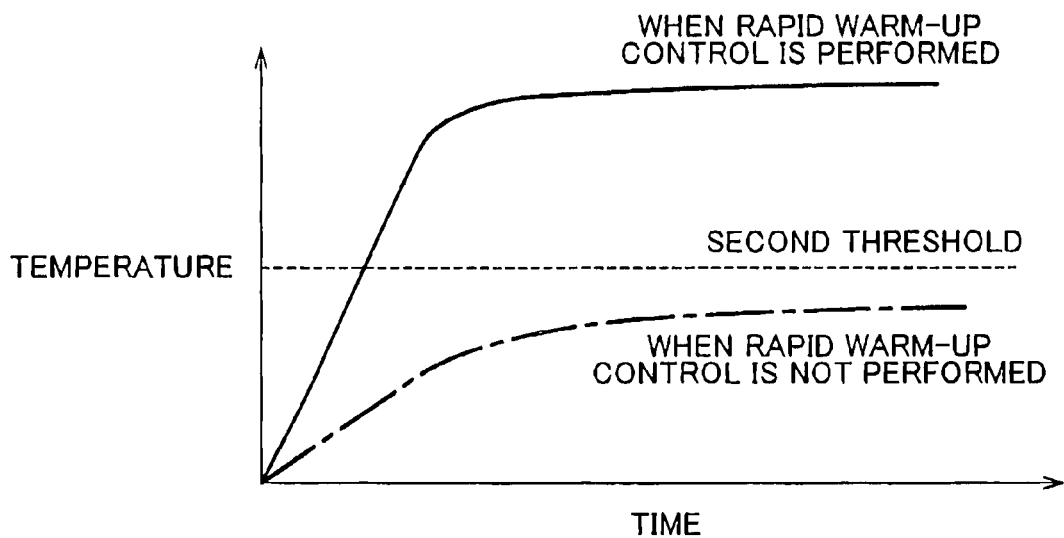
FIG. 7 is a chart illustrating how the temperature of the inner cover changes.

When the rapid warm-up control in which the ignition timing is retarded is being executed in order to warm up the catalyst 118 quickly while the temperature of the engine 100 is low, the temperature EXtemp of exhaust gas is high. In this case, as indicated by the solid curve in FIG. 7, the temperature Tsen of the wall surface of the inner cover 320 quickly increases and exceeds the second threshold.

On the other hand, when the driver is requiring acceleration of the vehicle by stepping down the accelerator pedal 142 sharply, execution of the rapid warm-up control is prohibited even if the temperature of the engine 100 is low. This is because the output of the engine 100 may decrease if the ignition timing is retarded in the rapid warm-up control. In this case, the temperature EXtemp of exhaust gas is low, and therefore the increase in the temperature Tsen of the wall surface of the inner cover 320 is sluggish as indicated by the one-dotted curve in FIG. 7.

However, in some cases, the temperature Texp of the exhaust port 114 may exceed the first threshold while the temperature Tsen of the wall surface of the inner cover 320 remains below the second threshold.

Therefore, the heating of the zirconia element 300 by the heater 310 (S130) is carried out when at least one of the condition that the temperature Texp of the wall surface of the exhaust port 114 is equal to or higher than the first threshold and the condition that the temperature Tsen of the wall surface of the inner cover 320 is equal to or higher than the second threshold is in effect (S120: YES).

As such, the A/F sensor 128 can be activated at the earlier of the time the temperature Texp of the exhaust port 114 reaches the first threshold and the time the temperature Tsen of the wall surface of the inner cover 320 reaches the second threshold. As a result, the A/F sensor 128 can be activated at an earlier time.

Conversely, if the temperature Texp of the wall surface of the exhaust port 114 is lower than the first threshold and the temperature Tsen of the wall surface of the inner cover 320 is lower than the second threshold (S120: NO), the heating of the zirconia element 300 by the heater 310 is prohibited (S140). This prevents the zirconia element 300 from being heated when there is a possibility that the zirconia element 300 would contact water droplets. As such, the zirconia element 300 is not damaged.

As described above, the ECU corresponding to the control apparatus of the first exemplary embodiment allows the zirconia element to be heated by the heater when at least one of the condition that the temperature Texp of the wall surface of the exhaust port is equal to or higher than the first threshold and the condition that the temperature Tsen of the wall surface of the inner cover is equal to or higher than the second threshold is in effect, and the ECU prohibits the heating of the zirconia element by the heater when the temperature Texp of the wall surface of the exhaust port is lower than the first threshold and the temperature Tsen of the wall surface of the inner cover is lower than the second threshold. As such, the A/F sensor can be activated at an earlier time without damaging the zirconia element.

Note that the temperature of the wall surface of the outer cover 330 may be used instead of the temperature of the wall surface of the inner cover 320.

Second Exemplary Embodiment

Next, the second exemplary embodiment of the invention will be described. The second exemplary embodiment is different from the foregoing first exemplary embodiment in that the zirconia element is heated when the count that is incremented by an amount set according to the temperature of exhaust gas reaches a third threshold. That is, other structures employed in the second exemplary embodiment are the same as those in the first exemplary embodiment, and they will not be described again.

The control algorithms of the programs executed by the ECU 200 that corresponds to the air-fuel ratio sensor control apparatus of the second exemplary embodiment will be described with reference to FIG. 8.

First, in S200, the ECU 200 determines whether the ignition timing of the engine 100 is earlier or later than a reference value. For example, the reference value is set to a value corresponding to the top dead center of the piston 110.

If the ignition timing of the engine 100 is earlier than the reference value (S200: EARLIER), the ECU 200 then proceeds to S210. Conversely, if later than the reference value (S200: LATER), the ECU 200 then proceeds to S220.

Figure 9:
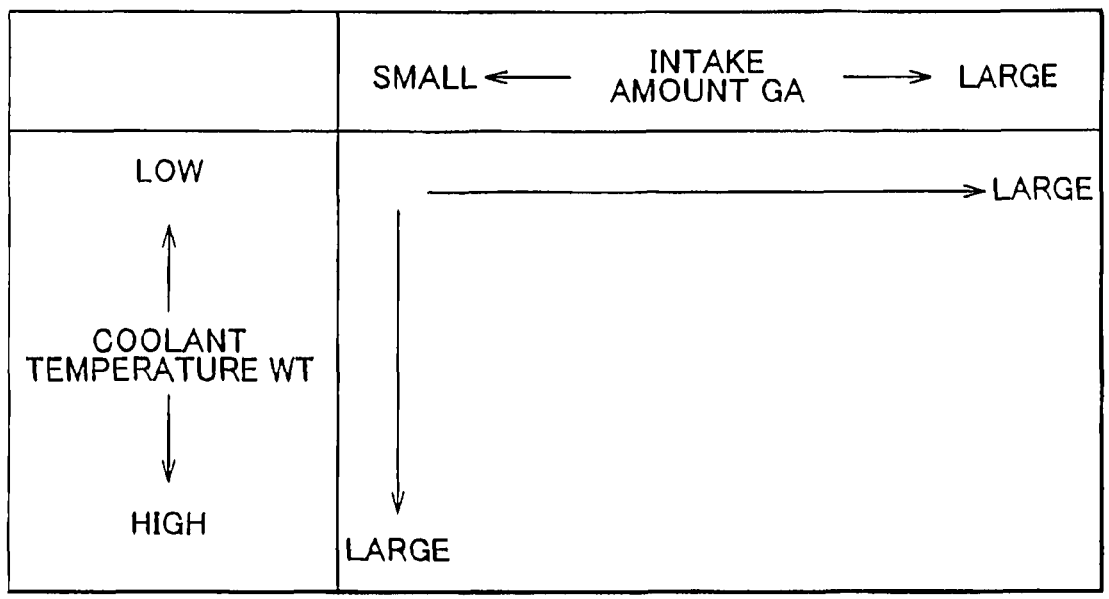
FIG. 9 is a first map that is used in the second exemplary embodiment to set the amount by which to increment the count of the counter.

In S210, the ECU 200 sets the amount by which to increment the count of the counter based on a first map which is shown in FIG. 9 and in which the amount GA of intake air for the engine 100 and the temperature WT of the coolant at the start of the engine 100 are used as parameters. The incremental amount of the counter is set larger as the amount GA of intake air for the engine 100 increases and as the temperature WT of the coolant increases.

Figure 8:
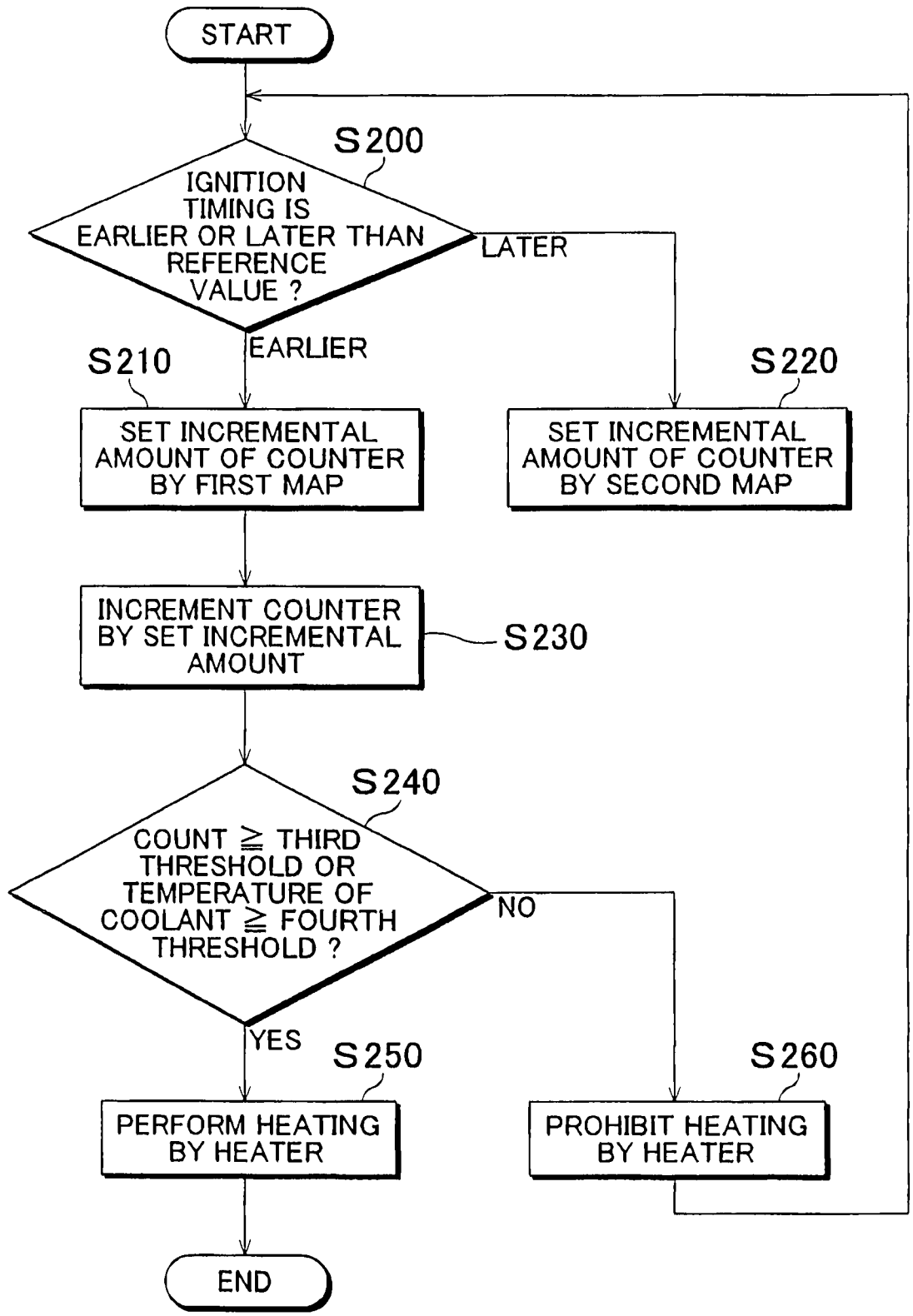
FIG. 8 is a flowchart illustrating the control algorithm of the program executed by the ECU of the air-fuel ratio sensor control apparatus according to the second exemplary embodiment of the invention.
Figure 10:
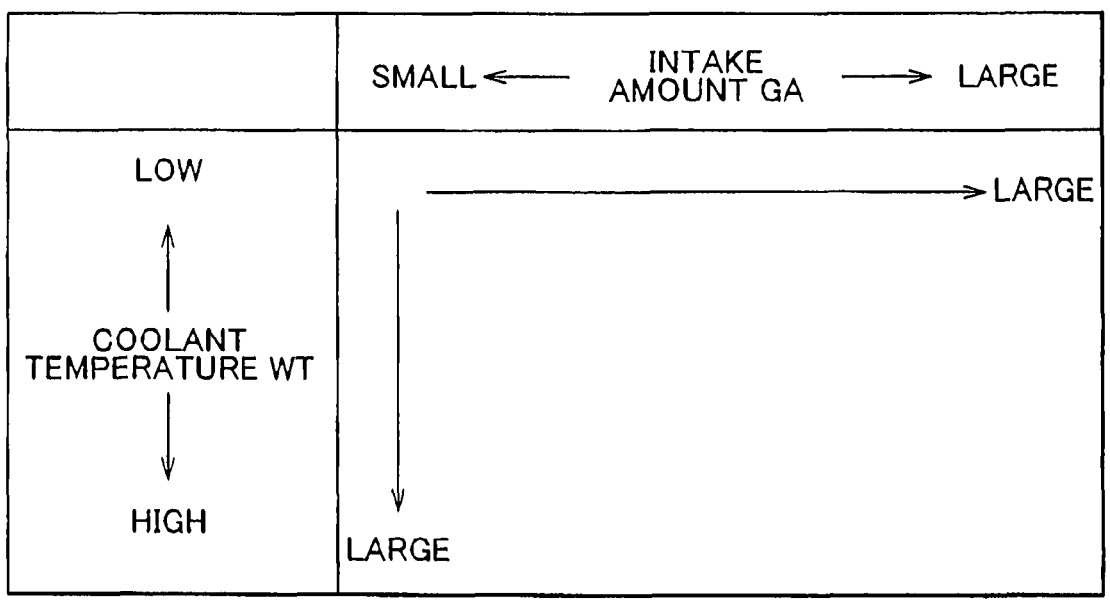
FIG. 10 is a second map that is used in the second exemplary embodiment to set the amount by which to increment the count of the counter.

Back to FIG. 8, on the other hand, in S220, the ECU 200 sets the incremental amount of the counter based on a second map which is shown in FIG. 10 and in which the amount GA of intake air for the engine 100 and the temperature WT of the coolant at the start of the engine 100 are used as parameters. The incremental amount of the counter is set larger as the amount GA of intake air for the engine 100 increases and as the temperature WT of the coolant increases.

The incremental amount of the counter set using the second map is larger than that set using the first map. That is, the incremental amount of the counter set by the second map is larger than that set by the first map, if they are set based on the same intake amount GA and the same coolant temperature WT.

Back to FIG. 8, in S230, the ECU 200 increments the count of the counter by the incremental amount set as described above. Then, in S240, the ECU 200 determines whether at least one of the condition that the count of the counter is equal to or lager than a third threshold and the condition that the temperature WT of the coolant is equal to or higher than a fourth threshold is in effect.

The third threshold is set such that the time needed for the temperature of the wall surface of the exhaust port 114 to reach the temperature reflecting the dew point of water droplets passes before the count of the counter exceeds the third threshold. The fourth threshold is set to a value at or above which the temperature of the wall surface of the 114 is considered to have reached the temperature reflecting the dew point of water droplets. The temperature reflecting the dew point used for setting the third threshold and the fourth threshold may be the dew point of the water droplets or above.

If at least one of the condition that the count of the counter is equal to or larger than the third threshold and the condition that the temperature WT of the coolant is equal to or larger than the fourth threshold is in effect (S240: YES), the ECU 200 proceeds to S250. If not (S240: NO), the ECU 200 proceeds to S260.

In S250, the ECU 200 heats the zirconia element 300 using the heater 310, after which the present cycle of the routine ends. In S260, on the other hand, the ECU 200 prohibits the heating of the zirconia element 300 by the heater 310, after which the ECU 200 returns to S200.

Next, a description will be made of the operation of the ECU 200 which has the foregoing structure and executes the control routine described above and which corresponds to the air-fuel ratio sensor control apparatus according to the second exemplary embodiment.

After the start of the engine 100, if the ignition timing of the engine 100 is earlier than the reference value (S200: EARLIER), the incremental amount of the counter is set using the first map in which the amount GA of intake air for the engine 100 and the temperature WT of the coolant at the start of the engine 100 are used as parameters (S210).

Then, the count of the counter is incremented by the set incremental amount (S230). Next, if at least one of the condition that the count of the counter is equal to or larger than the third threshold and the condition that the temperature WT of the coolant is equal to or larger than the fourth threshold is in effect (S240: YES), the zirconia element 300 is heated by the heater 310 (S250).

On the other hand, if the count of the counter is smaller than the third threshold and the temperature WT of the coolant is lower than the fourth threshold (S240: NO), the heating of the zirconia element 300 by the heater 310 is then prohibited (S260).

Meanwhile, when the ignition timing of the engine 100 is retarded, the temperature of the exhaust gas becomes high as compared to when the ignition timing is advanced. Therefore, the rate of increase in the temperature of the wall surface of the exhaust port 114 differs depending upon the ignition timing. To cope with such differences, when the ignition timing of the engine 100 is later than the reference value (S200: LATER), the incremental amount of the counter is set using the second map that sets the incremental amount to be relatively large (S220), and the count of the counter is then incremented by the incremental amount set using the second map (S230).

As such, when the temperature of the exhaust gas is high and therefore the temperature of the wall surface of the exhaust port 114 increases quickly, the count of the counter is made to reach the third threshold value in a shorter time. Thus, the heating of the zirconia element 300 can be started at an earlier time.

As described above, according to the ECU corresponding to the air-fuel ratio sensor control apparatus of the second exemplary embodiment, the incremental amount of the count of the counter is set larger when the ignition timing is later than the reference value than when the ignition timing is earlier than the reference value, and the zirconia element is heated using the heater when the count of the counter reaches the third threshold. Thus, when the temperature of the exhaust gas is high and therefore the temperature of the wall surface of the exhaust port increases quickly, the count of the counter reaches the third threshold in a shooter time. Thus, the heating of the zirconia element can be started at an earlier time.

It is to be understood that the invention is not limited to the foregoing embodiments that are only exemplary and are not restrictive. To the contrary, the scope of the invention, which is defined by the claims, is intended to cover all the arrangements and modifications within the scope defined and their equivalencies.

The invention claimed is:

1. A control apparatus for an air-fuel ratio sensor that is provided in an exhaust passage of an internal combustion engine and has a protection member covering a sensing element, comprising:
    a calculation potion that calculates the temperature in the exhaust passage and the temperature of the protection member, and
    a heating control portion that controls a heating device that is provided in the air-fuel ratio sensor to heat the sensing element, wherein
    the heating control portion controls the heating device not to heat the sensing element when the temperature in the exhaust passage is lower than a first threshold and the temperature of the protection member is lower than a second threshold and controls the heating device to heat the sensing element when the temperature in the exhaust passage is higher than the first threshold and/or the temperature of the protection member is higher than the second threshold.

2. The control apparatus according to claim 1, further comprising:
    an exhaust gas temperature estimating portion that estimates the temperature of exhaust gas of the internal combustion engine, wherein
    the calculating portion calculates at least one of the temperature in the exhaust passage and the temperature of the protection member based on the temperature of the exhaust gas.

3. The control apparatus according to claim 2, wherein the exhaust gas temperature estimating portion estimates the temperature of the exhaust gas based on the ignition timing of the internal combustion engine and the amount of intake air for the internal combustion engine.

4. The control apparatus according to claim 2, further comprising:
    a coolant temperature detecting portion that detects the temperature of coolant of the internal combustion engine, wherein
    the calculating portion calculates the temperature in the exhaust passage based on the temperature of the coolant of the internal combustion engine.

5. The control apparatus according to claim 1, wherein the first threshold is set to a temperature reflecting to a dew point of water in the exhaust passage.

6. The control apparatus according to claim 1, wherein the second threshold is set to a temperature that causes water to evaporate in a moment when the water contacts the protection member.

7. The control apparatus according to claim 1, wherein the internal combustion engine is controlled to warm up a catalyst provided in the exhaust passage by retarding an ignition timing at a low temperature.

8. A control apparatus for an air-fuel ratio sensor that is provided in an exhaust passage of an internal combustion engine and has a protection member covering a sensing element, comprising:
    an exhaust gas temperature estimating portion that estimates the temperature of exhaust gas of the internal combustion engine;
    a coolant temperature detecting portion for detecting the temperature of coolant of the internal combustion engine;
    a counter that increments a count according to the temperature of the exhaust gas; and
    a heating controlling portion that controls heating portion that heats the sensing element, the heating portion being provided in the air-fuel ratio sensor, wherein
    the heating controlling portion controls the heating portion to heat the sensing element when the count of the counter is larger than a third threshold and/or the temperature of the coolant is higher than a fourth threshold; wherein
    an amount by which the counter increments the count is set larger when an ignition timing of the internal combustion engine is at a first point than when the ignition timing is at a second point that is earlier than the first point.

9. The control apparatus according to claim 8, wherein the third threshold is a value that is set such that a time needed for the temperature in the exhaust passage to reach a temperature reflecting to a dew point of water passes before the count of the counter exceeds the third threshold.

10. The control apparatus according to claim 8, wherein the fourth threshold is set as a temperature of the coolant at which the temperature in the exhaust passage is estimated to reach a temperature reflecting to a dew point of water.

11. A control method for an air-fuel ratio sensor that is provided in an exhaust passage of an internal combustion engine and has a protection member covering a sensing element, comprising:
    estimating the temperature of exhaust gas based on the amount of intake air for the internal combustion engine and the ignition timing of the internal combustion engine;
    calculating the temperature in the exhaust passage and the temperature of the protection member based on the temperature of the exhaust gas;
    heating the sensing element when the temperature in the exhaust passage is higher than a first threshold and/or the temperature of the protection member is higher than a second threshold.

12. The control method according to claim 11, further comprising detecting the temperature of coolant of the internal combustion engine, wherein
    the temperature in the exhaust passage is calculated based on the temperature of the coolant and the temperature of the exhaust gas.

* * * * *